(12) United States Patent
Roessl et al.

(10) Patent No.: US 10,172,580 B2
(45) Date of Patent: Jan. 8, 2019

(54) PHASE RETRIEVAL FOR SCANNING DIFFERENTIAL PHASE CONTRAST SYSTEMS

(71) Applicant: KONINKLIJKE PHILIPS N.V., Eindhoven (NL)

(72) Inventors: Ewald Roessl, Hamburg (DE); Hendrik Albert Pastink, Eindhoven (NL); Thomas Koehler, Hamburg (DE); Heiner Daerr, Hamburg (DE); Udo Van Stevendaal, Hamburg (DE); Gerhard Martens, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 197 days.

(21) Appl. No.: 15/104,816

(22) PCT Filed: Dec. 3, 2014

(86) PCT No.: PCT/EP2014/076325
§ 371 (c)(1),
(2) Date: Jun. 15, 2016

(87) PCT Pub. No.: WO2015/090949
PCT Pub. Date: Jun. 25, 2015

(65) Prior Publication Data
US 2016/0317112 A1    Nov. 3, 2016

(30) Foreign Application Priority Data
Dec. 17, 2013   (EP) ..................................... 13197763

(51) Int. Cl.
*G21K 1/06*    (2006.01)
*A61B 6/00*    (2006.01)
(Continued)

(52) U.S. Cl.
CPC ................ *A61B 6/484* (2013.01); *A61B 6/03* (2013.01); *A61B 6/06* (2013.01); *A61B 6/4291* (2013.01);
(Continued)

(58) Field of Classification Search
None
See application file for complete search history.

(56) References Cited

U.S. PATENT DOCUMENTS 5,291,539 A    3/1994   Thumann
8,681,934 B2   3/2014   Nagai
(Continued)

FOREIGN PATENT DOCUMENTS

CN    101011250 A    8/2007
JP    2004313546 A   11/2004
(Continued)

OTHER PUBLICATIONS

Kottler, C. et al "Grating interferometer based scanning setup for hard x-ray hase contrast imaging", Review of Scientific Instruments, vol. 78, No. 4, pp. 043710-043714, 2007.
(Continued)

*Primary Examiner* — Hoon Song
(74) *Attorney, Agent, or Firm* — Larry Liberchuk (57) ABSTRACT

A phase contrast imaging apparatus (MA) and related image processing method. The imaging apparatus includes a movable arm (AR) that carries a detector (D) and one or more interferometric gratings (G0,G1,G2). The imaging apparatus includes a rigidizer (RGD) to control the rigidity of at least the arm (AR) or a mounting (GM) for the gratings (G0,G1, G2). This allows controlling a drift of a Moiré pattern as detected in a sequence of readouts. A phase of the so controlled Moiré pattern can be used to calibrate the imaging apparatus by using the image processing method.

13 Claims, 6 Drawing Sheets

(51) Int. Cl.
*G21K 1/04* (2006.01)
*A61B 6/03* (2006.01)
*A61B 6/06* (2006.01)

(52) U.S. Cl.
CPC .............. *A61B 6/502* (2013.01); *A61B 6/585* (2013.01); *A61B 6/587* (2013.01); *G21K 1/04* (2013.01); *G21K 2207/005* (2013.01)

(56) References Cited

U.S. PATENT DOCUMENTS

| | | | |
|---|---|---|---|
| 8,781,069 B2 | 7/2014 | Murakoshi | |
| 8,995,614 B2 | 3/2015 | Nagatsuka | |
| 2005/0175154 A1 | 8/2005 | Kondradsson | |
| 2007/0183583 A1* | 8/2007 | Baumann | A61B 6/032 378/145 |
| 2011/0235779 A1 | 9/2011 | Ishii | |
| 2012/0148021 A1 | 6/2012 | Ishii | |
| 2012/0288056 A1* | 11/2012 | Murakoshi | A61B 6/4233 378/37 |

FOREIGN PATENT DOCUMENTS

| | | |
|---|---|---|
| WO | 2012125086 A1 | 9/2012 |
| WO | 2013004574 A1 | 1/2013 |
| WO | 2014206841 A1 | 12/2014 |
| WO | WO2014206841 A1 | 12/2014 |
| WO | 2015044238 A1 | 4/2015 |
| WO | WO2015044238 A1 | 4/2015 |

OTHER PUBLICATIONS

Weitkamp, Timm et al "X-ray Phase Imaging with a Grating Interferometer", Optics Express, vol. 13, No. 16, pp. 6296-6304, 2005.

Tapfer, Arne et al "Experimental Results from a Preclinical X-ray Phase-Contrast CT Scanner", PNAS, vol. 109, No. 39, pp. 15691-15696, 2012.

Roessl, Ewald et al "Clinical boundary conditions for grating-based differential phase-contrast mammography", RSTA Royal Society 2014.

* cited by examiner

PHASE RETRIEVAL FOR SCANNING DIFFERENTIAL PHASE CONTRAST SYSTEMS

CROSS-REFERENCE TO PRIOR APPLICATIONS

This application is the U.S. National Phase application under 35 U.S.C. § 371 of International Application No. PCT/EP2014/076325, filed on Dec. 3, 2014, which claims the benefit of European Patent Application No. 13197763, filed on Dec. 17, 2013. These applications are hereby incorporated by reference herein.

FIELD OF THE INVENTION

The invention relates to a phase contrast radiography system, to method for processing data supplied by a phase contrast radiography system, to a computer program element, and to a computer readable medium.

BACKGROUND OF THE INVENTION

In some scanning imaging systems such as scanning mammography systems, the object to be imaged is scanned by movement of the imaging system's detector. Some of these scanning imaging systems include an interferometer arrangement that allows grating based phase contrast imaging. See for instance C. Kottler et al, "Grating interferometer based scanning setup for hard x-ray phase contrast imaging", Rev. Sci. Instrum. 78, 043710 (2007).

The proposition in phase contrast imaging is that radiation intensity as detected at the detector does not only encode information on absorption (traditional x-ray radiography is based on this) but also holds information on refraction experienced by the radiation in its passage through the object to be imaged. Phase contrast imaging then uses a number of techniques referred to as "phase retrieval" which is the task of extracting this refractive information from the detected signals.

It has been observed that, when a fixed interferometer setup is used, i.e., one where the gratings are fixed with respect to each other during image acquisition, calibration proves remarkably cumbersome. For instance, some approaches use specially designed phantom bodies.

SUMMARY OF THE INVENTION

There may therefore be a need for a different method and related system for phase contrast imaging to make the calibration procedure easier.

The object of the present invention is solved by the subject matter of the independent claims where further embodiments are incorporated in the dependent claims. It should be noted that the following described aspect of the invention equally applies to the computer program element and to the computer readable medium.

According to a first aspect of the invention, there is provided a phase contrast radiography system of the scanning type, comprising:
  a pedestal;
  an arm movable relative to the pedestal;
  in a mounting in or at the arm, an interferometer assembly including two or more gratings;
  an X-ray source for generating radiation;
  a detector movable in a scanning motion for receiving said radiation after interaction of said radiation with the interferometer gratings to produce a drifting Moiré intensity pattern detectable by the detector across a sequence of readouts when the apparatus is in use;
  a rigidizer operable to apply a force upon the arm and/or the interferometer mounting to vary prior or during said scanning motion the rigidity thereof so as to impart a relative motion between the at least two gratings thereby affording the ability to vary the local fringe phase of said Moiré pattern in a controllable manner.

By virtue of the rigidizer component, the imaging system as proposed herein allows to control the Moiré phase shift instead of depending on the particular amount of shift realized more or less by chance. Being able to control the Moiré phase shift has the advantage that detector calibration operation for phase retrieval purposes can be rendered more stable. The system designer has better control of how quickly the Moiré pattern drifts, which impacts the stability of a calibration procedure, in particular the one proposed herein. In particular, in the proposed calibration, it is desirable to have the Moiré pattern drift at least by a full period during the scan motion. On the other hand, if the pattern drifts too quickly, this may incur a loss of visibility, which may degrade overall image quality.

For example, it might be useful to change the level of total fringe phase shift slightly between medio-lateral-oblique (MLO) view where the arm is at an average angle of around 40%-50% from the vertical and a CC view where the gantry is at an average angle around the vertical direction. An otherwise uncontrolled Moiré phase shift might depend on the effects of gravity on the various components which will be different for various angular positions.

According to one embodiment, the rigidizer is arranged as clamp actuator with at least one pair of jaws for engagement therebetween of the arm and/or the interferometer assembly so as to allow selectably adjusting an amount of the applied force so as to achieve a desired amount of drifting of the Moiré pattern.

According to one embodiment, the rigidizer is manually operable.

According to one embodiment, the clamp actuator includes a micrometer arrangement with one or more calipers operable to engage the mounting so as to allow a user to selectably adjust in discrete steps an amount of the applied force.

Because the adjustability is restricted to discrete steps, different rigidity settings are reproducible which in turn ensure consistent image quality.

According to one embodiment, the rigidizer is formed from a bimetallic sheet attached to the arm and/or the interferometer mounting.

According to one embodiment, the system comprises a video signal generator. Said video signal generator is operative to supply the sequence of readouts to a display unit during operation of the rigidizer so as to achieve a visual rendering of how the Moiré phase varies with the applied force. This allows the operator to easily select certain preferred rigidity settings.

According to another aspect of the present invention there is provided as a method for processing data supplied by a phase contrast radiography apparatus of the scanning type including an interferometer, the method comprising the steps of:
  receiving a sequence of detector readouts that together record a drifting Moiré pattern, the readouts detected by a plurality of detector pixels of a detector of said apparatus during a blank scan operation, the drift caused by relative motion between at least two gratings of said interferometer during said scan operation;

fitting the readouts to a measurement signal model function $f$ by solving for a plurality of calibration parameter including a plurality of phases ($\varphi_j$) of the drifting Moiré pattern and/or at least one of i) intensity ($A_i$) per pixel and ii) visibility ($V_i$) per pixel.

The method allows a calibration task to be carried our more efficiently. Before a phase retrieval can be done, one must acquire some base line data to learn about calibration parameter, that is, individual characteristics or pixel specific behavior of detector pixels. This has been done in the past by using specific phantom bodies that are placed in the examination region instead of the breast. In the present approach however it is proposed to acquire those base lines in a calibration step solely on the basis of a blank scan.

In other words, it is proposed herein to harness an otherwise undesirable effect, namely the Moiré pattern drift, to derive the (in the first place) unknown phase information of the Moiré pattern by enlarging the "pool" of variables and by now solving for the phase drift variables $\varphi_j$ when fitting readouts. This affords the determination of the phase of the Moiré pattern without use of either dedicated phantoms or without knowledge about the absolute position of the gratings with respect to each other.

According to one embodiment, the fitting operation includes solving for a pixel displacement ($\Delta_i$) per pixel. In other words, the signal function model is augmented by the pixel displacements that model imperfections of pixel arrangements in the detector. This further increases the pool of fittable variables thus allowing to model deviations of the typical purely sinusoidal Moiré pattern, as they might occur due to imperfections of the gratings.

The fitting problem may be formulated into objective function which can then be optimized to accomplish the fitting operation. Suitable optimization algorithms include downhill simplex algorithm, conjugate gradients or others may be used.

According to one embodiment, the method further comprises the step of:

adjusting the rigidity of the arm and/or of the mounting therein of the interferometer so as to control the amount of drift in the Moiré pattern. This can be done by using the imaging apparatus as proposed herein having the rigidizer.

According to one embodiment, the method further comprises the step of:

applying a phase retrieval operation to the detector readouts for the blank scan to produce at least one corrector phase contrast image. In other words, the detector readouts for the blank scan are treated as if they were obtained in an object scan. In the blank scan, there is no object placed between radiation source and detector whereas in an object scan there is. Applying the phase retrieval includes in particular re-grouping (or re-sampling or re-sorting) of the blank detector readouts into groups according to projection direction though the image space, that is, the space between X-ray source and the detector.

According to one embodiment, the method further comprises the steps of:

scanning an object to be imaged to obtain detector readouts for the object;

using the at least one corrector phase contrast image in applying a phase retrieval operation to the object detector readouts to obtain a phase contrast image of the object.

BRIEF DESCRIPTION OF THE DRAWINGS

Exemplary embodiments of the invention will now be described with reference to the following drawings wherein.

DETAILED DESCRIPTION OF EMBODIMENTS

Figure 1:
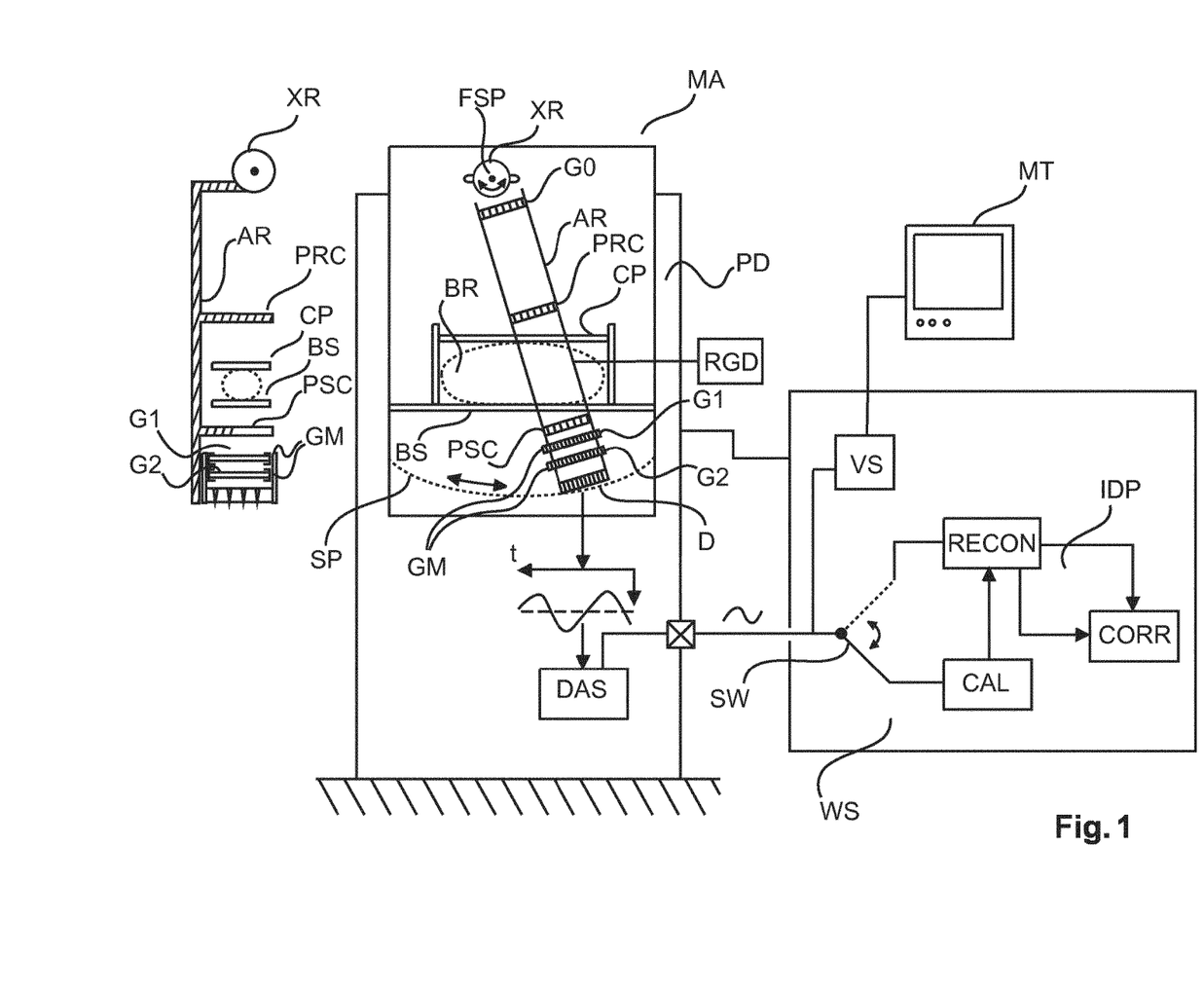
FIG. 1 shows an imaging arrangement.

With reference to FIG. 1 there is shown a phase contrast imaging radiography apparatus MA. In one embodiment the phase contrast imaging apparatus is a mammography apparatus of the scanner type but it will be appreciated that the following finds equal application to other scanning radiography imagers for phase contrast imaging for instance, computed tomography CT scanners. It will be appreciated that the term "arm" as used herein corresponds to the rotatable gantry in CT scanner systems.

The imaging system MA is connected via suitable interface means and across a communication network to a workstation WS. In general, workstation WS is a computing system with which a clinician ("user") is able to control operation of the imaging system. According to one embodiment, there is also a display unit or monitor M which is controlled by work station WS and which allows displaying of images that are acquired by the imaging system. Workstation WS runs an operating system which in turn controls execution of an image data processor IDP including a number of modules CAL, RECON and CORR whose operation will be explained in more detail below.

The mammography apparatus MA includes a pedestal PD on which there is mounted an x-ray source XR. The x-ray source is rotatable around its focal spot FSP. The pedestal PD supports a rotatable gantry with a rotatable hollow arm AR. The arm AR is rotatable around the focal spot FSP. The arm includes two or more interferometric gratings (a source grating G0, and a π-phase grating G1 and/or an analyzer grating G2) that together afford the phase imaging capability as will be explained in more detail below. G1 may also be a π/2-phase grating or other suitable phase grating. It is even possible, though not preferred, to use an absorber grating for G1 instead of a phase grating which is the preferred embodiment in medical applications but the absorber version for G1 may be called for in non-medical contexts.

At the lower end of the arm AR there is mounted a detector plate D with a radiation sensitive surface for detecting radiation emitted by source XR. The lower part of the arm also includes a gratings mounting GM itself mounted on top of the detector plate. The mounting holds one or two (preferably two) gratings G1,G2, with G1 on top of G2, and both above the detector plate, in particular, both gratings mounted above the radiation sensitive surface of the detector plate D. Source grating G0 is arranged at the upper end of the arm at an exit window of x-ray source XR. Also included in one embodiment and carried by the arm is a multi collimator arrangement preferably a pre-collimator PRC and a post collimator PSC. The post-collimator acts to remove scattering but this component may be left out in certain embodiment, as the G2 grating likewise acts to remove scattering.

There is an examination region defined as recess in a housing of the mammography apparatus MA for positioning into a sample object to be imaged, for instance the patient's breast BR. Part of the mammography apparatus MA housing defines a detector housing whose upper surface serves as a breast support BS on which patient's breast BR is placed during an imaging session, the breast support thereby delimiting from below the examination region. There is also a compression plate CP or paddle which can shuttle up and down to compress the breast when placed on the breast support.

In addition to the arm being rotatable as described above, it is also the whole gantry that is rotatable around a pivot point roughly at the height of the breast support. The whole gantry can thereby be tilted to change approach angle to so afford selectively imaging at different views, for instance at CC (cranio-caudal) view (at 12 o'clock position) or MLO (mediolateral oblique) view at about 2 o'clock position.

Radiation emitted by the source XR enters the arm through an exit window and then passes through the arm towards the detector. In its passage the radiation wave interacts with the first grating G0, also referred to as the source grating G0, to establish coherence.

Briefly, the radiation flow is as follows: the radiation wave is collimated by the one or two collimators, then interacts with the breast BR if present in the examination region, thereafter interacts with the two gratings G1,G2 and is then incident on detector plate D to be detected.

The mammography apparatus MA is operable in two basic modes: in a blank scan mode or in an object scan mode. When in object scan mode, which is the usual mode of operation, the user's breast BR or other sample is placed in the examination region. In blank scan mode, no object or breast is present in the examination region. In object scan, detector readouts are acquired, which can be fed into a reconstructor RECON to compute the phase contrast projection image (and, if desired, a (traditional) absorption contrast image and/or a small scattering ("dark field") contrast image) in a phase retrieval operation. For the phase reconstruction to work, one needs certain calibration parameter or data, in particular but not only, pixel specific characteristics. The calibration data is computed by a calibration module CAL from detector readouts acquired during the blank scan. Operation of calibrator module CAL and reconstructor module RECON will be explained in more detail below at FIG. 6. Both modules are envisaged to run on workstation WS.

During an object or blank scan, the lower part of the arm (and with it the detector plate and the gratings mounting GM) is motorized to move in the detector housing under breast support BS. The very left of FIG. 1 shows arm AR in side elevation with its components dependent therefrom and mounted therein or—thereon. In either mode, object or blank scan, the arm is moved in synchrony with the x-ray source rotation around its focal spot FSP so that the detector plate together with the gratings G1 and G2 traces out a scanner path SP under the breast BR, if present. In generally the scan path is an arc as shown in FIG. 1.

Figure 2:
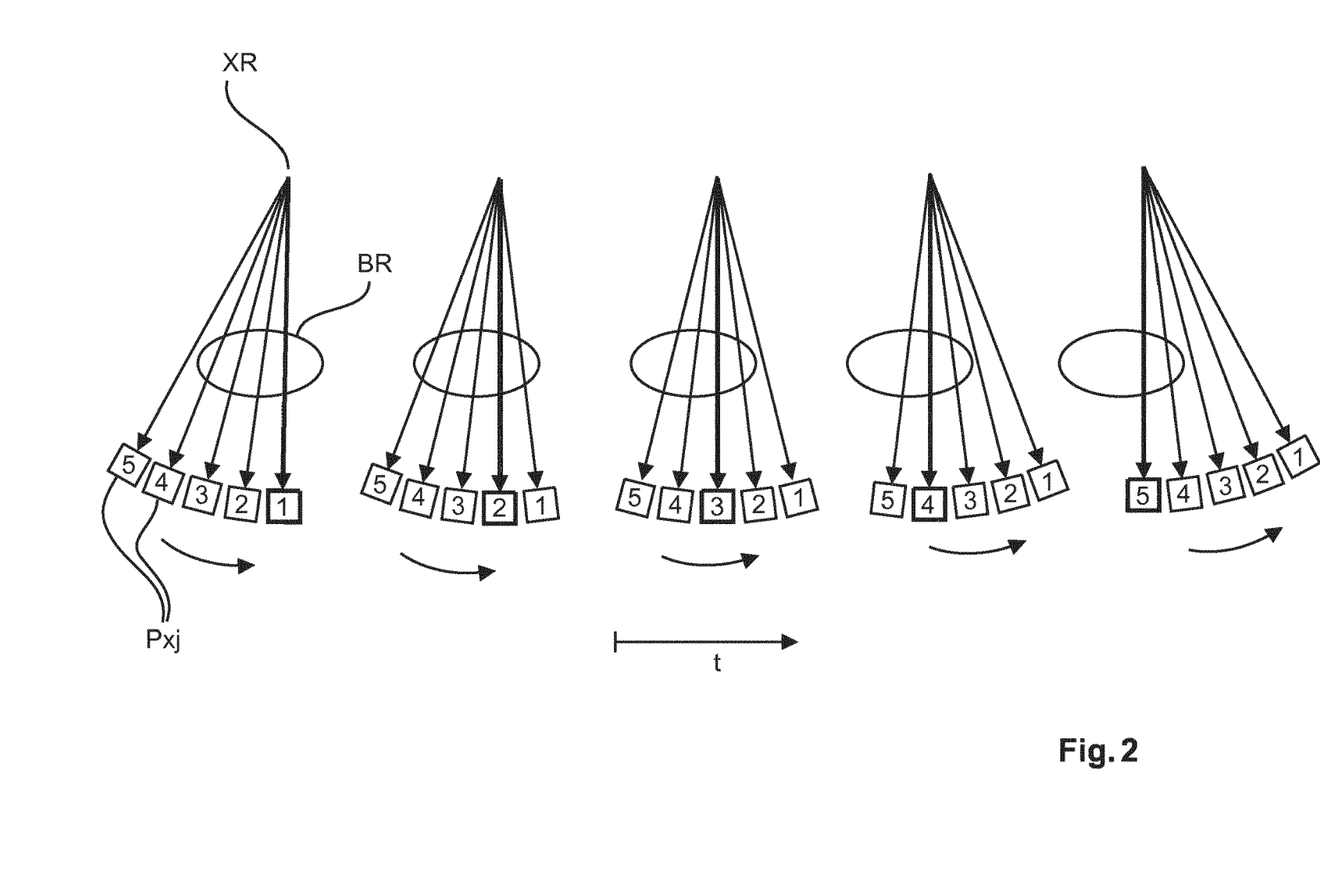
FIG. 2 shows a scanning operation of the imaging arrangement of FIG. 1.

In one embodiment the mammography apparatus MA is a single or multi slit system. In other words the detector plate D's radiation sensitive surface is formed from a single or in general a plurality (for example 8) semi-conductor detector lines deposited on a wafer substrate obtained by a photo-lithographic process or other suitable detector manufacturing technique. In the central, frontal elevation of FIG. 1, those detector lines DL or stripes extend into the paper plane arranged side by side. Each detector line is made up of a linear sequence of detector pixels. Because of the pre- and post collimator arrangement, the x-ray beam is essentially split up into a plurality of mini fan beams, with each fan beam irradiating at any one time exactly one of the respective detector lines, namely the one that happens to pass through said fan beam during the detector's motion. Said differently, the detector lines are being exposed to their respective mini fan beam, with each respective mini-fan beam changing direction during the scan. Whilst travelling along the scan path, each detector line will produce the respective readout at different positions on the path. In other words, unlike for 2D scanners, where the whole field of view acquired in a single snapshot, in the present multi-slit system, after complete the scanning motion, the successive readouts of the detectors during the scan can be used to compose a single 2D image for the field of view. FIG. 2 schematically shows the inherent redundancy (which equals the number of detector lines being on the order of 20 in one embodiment) in the multi-slit scanning approach. The detector lines (numbered 1-5) extend into the paper plane transverse to the scanning direction. By "readouts" as used herein is meant data collected by pixels along a given detector line when said detector line is at a given position l on the scan path. Put differently, the readouts are per detector line position.

The local position of each pixel or line can be specific by two "coordinates", column or line index and the pixel index. Because the pixel width, inter-pixel and inter-line distances are known and so is the position of the detector plate at any instance on its path SP, each detector readout (that is pixel response) can be "spatially stamped" by a tracker (not shown) so each detector readout can be associated with a specific one of a fixed geometrical ray that can be thought of to extend from the focal spot FSP across the examination region to the detector plate D. There is a plurality of such geometrical rays, and to each point in the examination region there is such a geometrical ray that passes through said point the plurality of rays forming a cone with the focal spot FPS as apex. One such geometrical ray is shown in FIG. 2 in bold. The spatial stamps associated with the readouts allow resolving this redundancy as will be explained in more detail at FIG. 6 when explaining operation of the reconstructor RECON.

The present mammogram apparatus uses phase contrast imaging in other words the contrast of the images produced by a said imager do not rely solely on absorption as is the case for conventional x-ray systems, but also relies on contrast that results from phase shifts which the radiation wave front experiences when interacting with the matter in the breast. The phase shifts or wave distortions are caused by locally different refractive behavior of the imaged matter.

However, the phase shifts themselves cannot be detected by the detector due to a lack of sufficient spatial resolution. Instead, the phase shifts are derived indirectly by using the interferometric gratings to sample a spatial pattern, a Moiré image pattern that is, detectable after proper setup along detector lines. Moiré patterns occur when the periodicity of the interference fringes is slightly and controllably different from the periodicity of the structures of the analyzer grating G2. This is the approach taught by A. Momose et al in "High-Speed X-ray phase imaging and X-ray phase tomography with Talbot interferometer and white synchrotron radiation" in Optics Express, Vol 17, No 15, pp 12540, (2009). First, as a function of the average wavelength of the radiation emitted by source XR and suitably chosen respective periodicities p0, p1, p2 of gratings G0-G2, collimators and gratings are carefully tuned in respect of the detector lines to a desired Talbot distance of desired order by aligning in orientation and distance. See for instance, see T. Donath et al in "Inverse geometry for grating-based x-ray phase-contrast imaging," J. Appl. Phys. 106, 054703 (2009). By then carefully de-tuning this Talbot set-up, for instance by varying the distance between the source grating G0 and the π-phase grating G1 (or π/2-phase grating) a reference Moiré pattern emerges along the detector lines during a blank scan. How this reference Moiré pattern is detected depends on the local characteristics of the various detector pixels as mentioned earlier in connection with the calibration data. The proposition is then, that an intervening object BR in an object scan will disturb this Moiré pattern. The disturbance shows as a phase shift of the reference Moiré pattern and this Moiré pattern phase shift is known to be related to the local gradient of the phase shift experienced by the wave when passing through object. So we need to know the phase ("reference phase") of the Moiré pattern to be able to perform phase retrieval. Determination of said Moiré phase reference is part of the calibration task summarized above.

In previous phase contrast imaging approaches, a fixed interferometric set-up has been used wherein, for phase retrieval purposes, one of the gratings is moved relative to the other to sample an interference pattern by "phase stepping". See for instance T. Weitkamp et al in "Optics Express", vol 13, No 16, pp 6296-6304 (2005). However, in the present approach no such phase stepping is needed. Instead, the phase retrieval operation is based on the scanning motion (together with the gratings motion) that is used herein to analyze the Moiré pattern fringes as recorded by detector during its motion to derive desired phase contrast information (and, incidentally, also the absorptive or dark field image which may be of use). So the detector motion serves to functions: first, it allows obtaining the full field of view—this was the original purpose—and second, the motion is harnessed for phase retrieval purposes.

However, the redundancy in the readouts adds a layer of complication. Because of the scanning motion, the Moiré pattern is not only distributed in space along a detector line but is also distributed in time across the various detector readouts from different positions along the path. Before turning to the operation of the calibration model CAL in more detail, certain characteristics of the blank scan detector readouts will now be examined in more detail with reference to FIGS. 2 and 3. Assume for a moment that in FIG. 2 no object is present as is the case in the blank scan. As the detector advances along its scan path, a certain detector line, say line 5 in FIG. 2, will receive radiation from the x-ray source and the reference Moiré pattern will emerge along the pixels $px_k$ of said detector line 5 (the detector line in the view of FIG. 2 extend into the paper plane). One may then expect that the Moiré patterns at each readout instance would be the same. After all, one may reason, the radiation merely passes through air which should be the same for any detector line no matter its position on the scan path. Albeit, this is not the case. Instead, what Applicant observed is that the Moiré pattern as seen by the very same detector line during the course of the scan motion is not the same. This is illustrated in FIG. 3.

Figure 3:
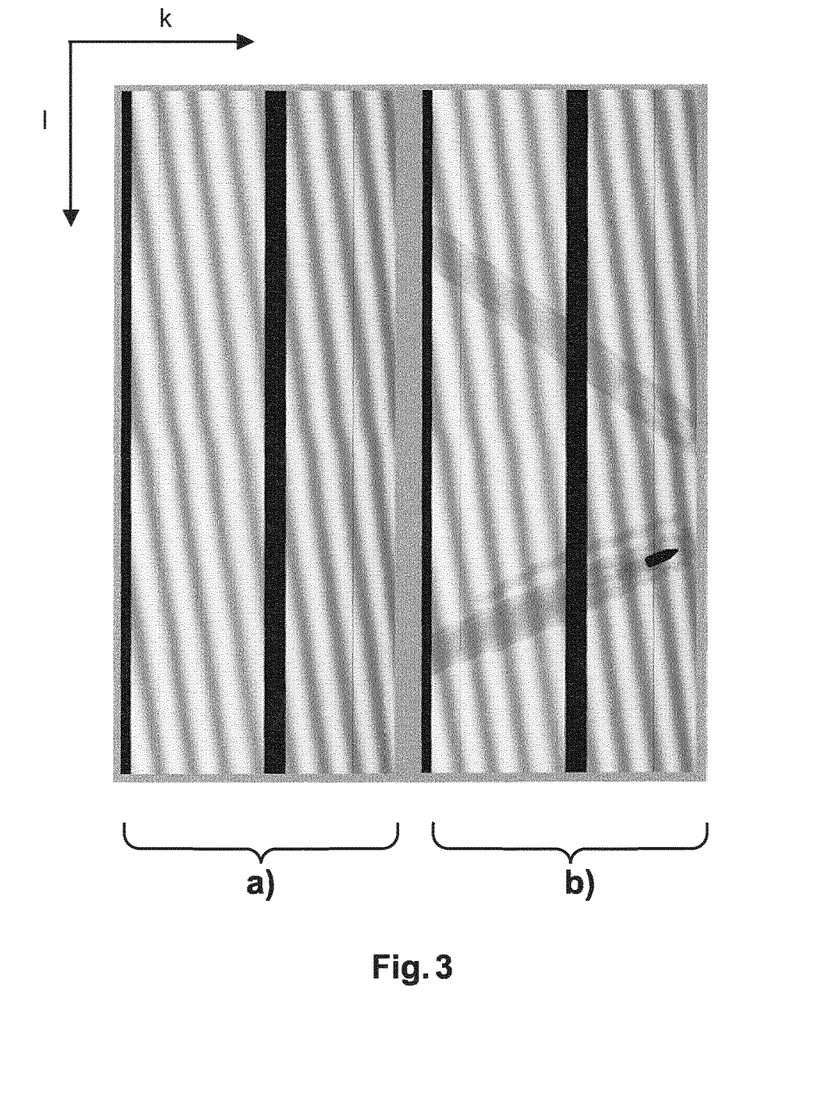
FIG. 3 shows detector readouts of a detector line.

The left pane in FIG. 3a shows a readout time l versus detector line measurements where k indicates pixel positions in a certain single line. There is a drift across the various readout instances as can be seen by the dark and white bands which run slanted across the pane defined by the plurality of readouts as per FIG. 3. The right hand side pane in FIG. 3b shows the same wide drift during object scan and the remarkable fact that the drift reproduces well for blank and object scan. About half way through along the readout direction l there can be seen a "kink" which indicates the instance when the scan arm AR moved across the horizontal position. Applicants observed that this Moiré drift can be attributed to mechanical imperfections in the rigidity of the scan arm AR. In other words, the arm AR and therefore the gratings mounting GM arranged in same slightly give during the scan arm motion for lack of rigidity. The broad, dark bands that run vertically stem from the readout electronics that are deposited in one embodiment on the detector lines so no radiation can be detected there. For instance, the back bands demark the footprint of an ASIC or other electronic component. However, the presence of those black bands is exemplary only as in alternative embodiments the readout electronics component is not positioned on the detector lines.

It is proposed herein to formulate a signal model function that accounts for said Moiré pattern drift. More particularly, it is proposed to not only include the detector specific quantities which one wishes usually to determine in a blank scan calibration but also to augment this model by including unknowns of the Moiré pattern drift and thereby enlarging the pool of variable to fit to so achieve a more stable estimation. The following modeling is the same for each detector line, so we will drop the line index in the following in the interest of a compact notation. Let us denote the measured intensities of one detector line during the scan with $I_{kl}$, where k is the detector column index and l the readout index. Let us first describe a simple version of the idea in order to illustrate the basic concept. In this simplified version, the Moiré pattern measured by $I_{kl}$ is modeled to follow the signal function:

$$I_{kl}=A_k(1+V_k \cos(\kappa k+\varphi_l)) \quad (1)$$

The signal model function as per (1) includes two parameters, namely $A_k$ and $V_k$, which are characteristic for the detector and the local properties of the gratings. The parameter $A_k$ relates to the product of the incoming intensity and the sensitivity of the detector pixel k, and the parameter $V_k$ relates to the local fringe visibility for the detector pixel k. Since these two parameters are detector and grating specific parameters, they do not change with the readout index l so instead they depend only on pixel position k. Changes of the fringe pattern during readout are completely attributed to a simple phase shift of the fringe pattern, represented by the readout-specific phases $\varphi_l$. Finally, the model contains also the global parameter κ, related to the spatial frequency of the Moiré fringes as detectable along the detector lines. In a system without any drift of the Moiré pattern, all phases $\varphi_l$ would be the same. By ensuring that the drift covers a few periods of the Moiré pattern over each detector pixel during the scan, a stable estimate of $A_k$ and $V_k$ can be achieved.

However, as can be seen the amount of drift is more or less at the whim of the instant configuration of the imager's arm AR and a certain given rigidity which is usually beyond the system designer's control. It is proposed herein to change this and to furnish the mammography apparatus MA with mechanical means, a rigidizer RGD, to be able to control the rigidity in particular of the scanner arm AR and all the gratings mountings GM by suitable mechanical action.

Figure 4:
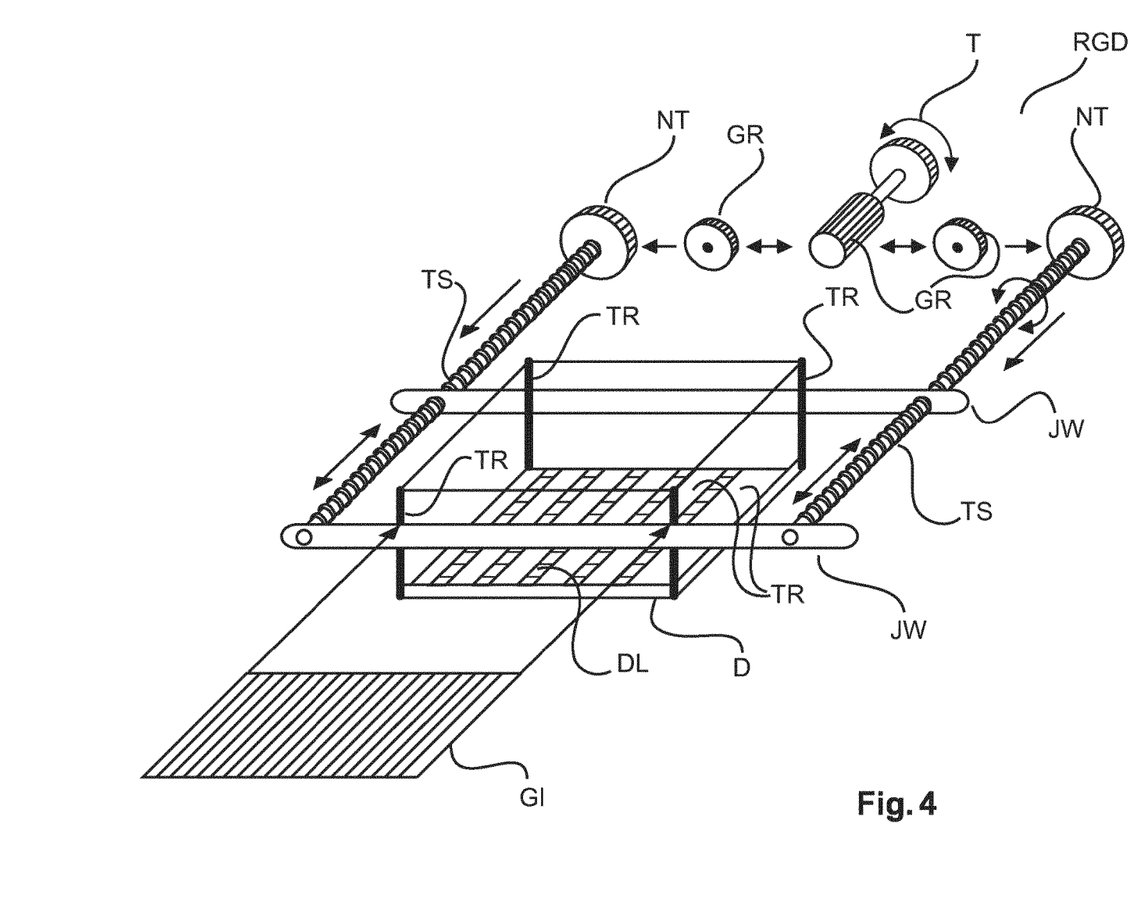
FIG. 4 shows a first embodiment of a component of the imaging arrangement of FIG. 1.

FIG. 4 shows one arrangement for controlling directly the stiffness of the gratings mounting GM as arranged in the scanner arm AR. FIG. 4 shows a perspective view on the gratings mounting GM which in one embodiment is a frame (made from steel in one embodiment) mounted on detector plate D. In the exemplary embodiment of FIG. 4, four detector lines DL are shown deposited on the detector plate D. Broadly, the arrangement of rigidizer RGD can be thought of as a lead screw arrangement. There is a set of jaws JW that embrace the gratings mountings cage GM from two sides. At either end of the two jaws, a threaded shaft TS is passed through corresponding eyelets in the jaws and is rigidly connected therewith. A guide nut NT is mounted on respective ones of the threaded shafts and can be advanced along the shaft towards respective ones of the jaws JW by operation of a suitable gearing arrangement GR that acts to inter-mesh said nuts and with a thumb wheel T which is user operable. In operation, the user turns the thumb wheel T and thereby effects advancing the engager nuts NT along their respective threaded shaft to force each into engagement with the respective ones of the jaws JW. This allows the user to apply a force onto the cage GM and essentially compress same thereby changing the rigidity of the grating mounting GM. According to one embodiment there is a ratchet mechanism interposed between the gear meshing and the thump wheel T to ensure that the force applied to cage GM is at discrete steps only and cannot be changed continuously. This ensures higher reproducibility of a certain Moiré pattern that is associated with a certain application of force. Also shown in FIG. 4 are track arrangements TR formed in cage GM in which the gratings G1 or G2 (in the Figure, merely one grating G1 is shown for ease of representation) are slideably received, not unlike slides in a slide projector. However it should be understood that the rigidizer that directly acts on the grating mounting cage GM can take numerous forms and FIG. 4 is merely one embodiment. Although the embodiment as per FIG. 4 is for manual operation, a motorized version is also envisaged with a controller that acts or varies the rigidity in response to an input. Also in, FIG. 4, both nuts NT move in synchrony when operating the thumbscrew T. This is but one embodiment however as other embodiments are envisaged where each nut can be actuated independently from the other, which applies to both, the manual and motorized version. For instance, a micrometer arrangement is also envisaged, where a micrometer type device is positioned so that the cage GM comes to lie between the two calipers. Operating the micrometer's thimble advances the spindle and the gratings cage GM is engaged between the calipers to apply a compression action thereon. Again, a suitable ratchet type mechanism can be arranged so as to ensure that the application of the force is constrained in a metered, graduated fashion into discrete steps.

Figure 5:
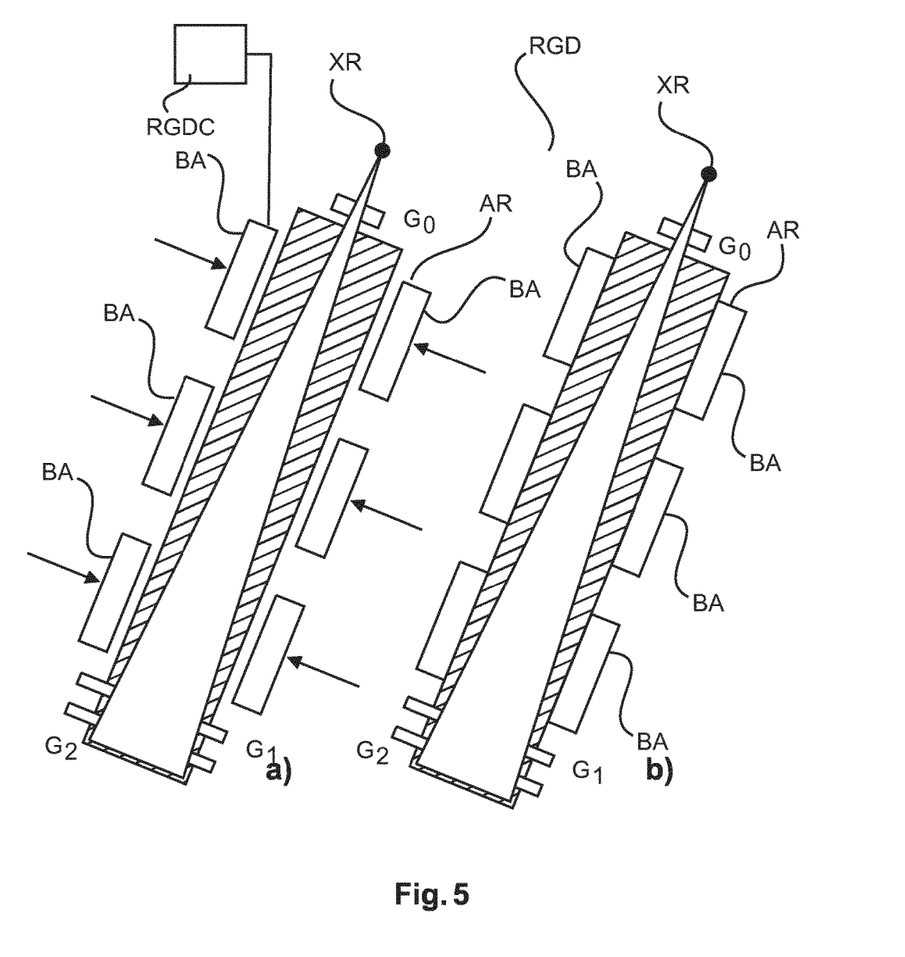
FIG. 5 shows a second embodiment of a component of the imaging arrangement of FIG. 1.

FIG. 5 shows an alternative embodiment which can be used instead or in addition to the embodiment in FIG. 4. In FIG. 5 the rigidizer RGD acts indirectly on the grating mountings cage by having actuators BA arranged on either side of the arm AR. In other words, in FIG. 5 the rigidizer acts directly on the arm to change the arm rigidity. FIG. 5a shows actuators BA, for instance bar elements arranged in a suitable number (one or more—three are shown as a non-limiting example) of pairs along the length of the arm AR. Upon actuation of actuators BA, a force is applied on the arm AR at respective locations to thereby change the overall rigidity of the arm AR. The different sets of actuators are either operable in synchrony or may also be operable independently thereby affording a higher degree of customized ability of the rigidity.

In another embodiment, bimetallic foil is used. One side of said foil is attached by bonding to the arm AR, either one the inside or outside. The arm is essentially "wrapped" in or lined with said foil. The bimetallic metal is then heated to various temperatures (before the scan due to account for a certain thermal inertial) which will then either increase or decrease the susceptibility of the arm to bending due to changes in gravitational torques during the scan.

In one embodiment, operation of rigidizer occurs during the actual scanning motion as opposed to a pre- or post scan adjustment that is also envisaged. In one embodiment, a rigidizer controller RGDC operates rigidizer RGD automatically. For instance, as observed earlier in connection with FIG. 2, the amount of Moiré pattern phase shift is an indicator for the rigidity or lack thereof. The readouts as per FIG. 2 for a certain detector line can be fed into controller RGDC. Controller RGDC then operates actuators BA to dynamically increase/decrease rigidly in dependence on the detected Moiré phase drift amount as per the detector readings. A large change will attract an application of a larger force to maintain rigidity whereas force application can be relaxed otherwise. Controller may thus operate in a closed loop manner to increase or decrease force to maintain a desired Moiré pattern shift or to ensure that this shift remains below a user-definable threshold.

In an alternative embodiment or in addition to monitoring readouts to determine the amount of force (or heat as the case may be per the bimetal embodiment) to be applied, rigidizer's operation may be linked to certain positions of the detector plate on path SP. For instance, as observed earlier, there is a kink in phase Moiré change at passage of arm AR through the vertical position. This may be an instant then when a larger rigidity is called for. Operation of controller RGDC may therefore be programmed to such that force is applied in response to the arm's AR position along its path SP in particular force is applied when arm assumes a vertical position.

Also it might be useful to change the level of total fringe phase shift slightly between MLO view where the gantry is at an average angle of around 40%-50% from the vertical and a CC view where the gantry is at an average angle around the vertical direction. Controlling the shift by rigidizing the arm or cage GM will offset for otherwise undesirable shift effects caused by gravity on the various components which will be different for various angular approach positions for different views.

According to one embodiment it is envisaged that the respective readout during operation of the rigidizer are rendered for view on a screen which allows the user to directly examine how the Moiré pattern changes whilst varying the force. In one embodiment a graphic representation of the moray pattern drift is shown in FIG. 3 and can be rendered for view on a screen.

We turn to the processing of the detector readouts. Broadly as will be explained in more detail below, the calibration data is acquired by having the detector readout in a bank scan processed by a calibration unit CAL. The calibration data is then passed to re-constructor RECON, which then operates to perform a phase retrieval step to produce inter alia the phase contrast image and/or an absorption and/or a scatter image.

Figure 6:
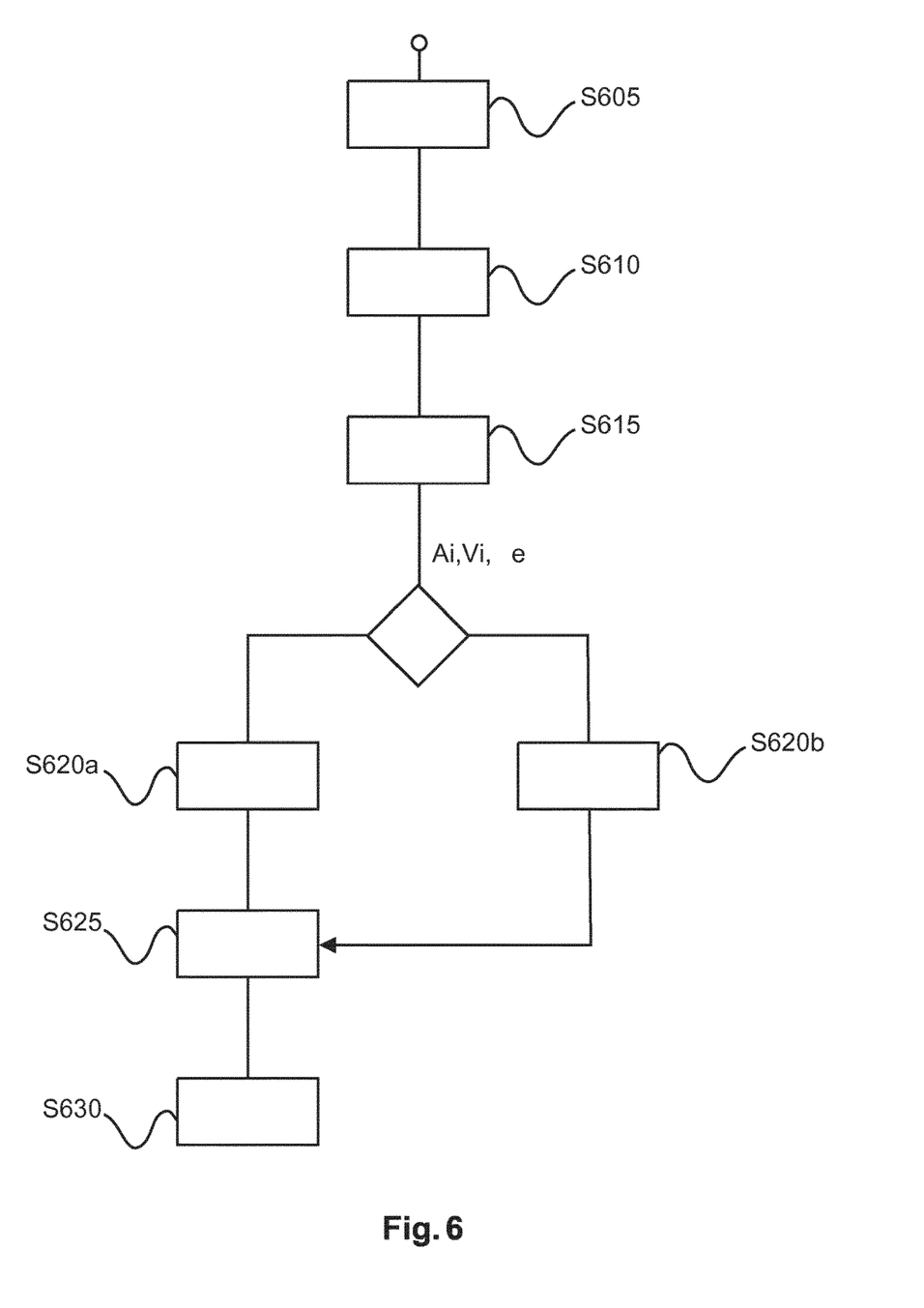
FIG. 6 shows a flow chart of an image data processing method.

Turning now first to the operation of calibration module CAL, reference is now made to flow chart in FIG. 6. At step 605 the rigidity of the arm AR and/or the gratings mounting GM is adjusted to the desired degree of rigidity.

At step 610 a blank scan is then carried out with the arm now having the desired rigidity. Each pixel responds by issuing an electrical signal that depends on the radiation intensity seen by the respective pixel at an instance and/or position along the scan path. The collection of these electrical signals is then A/D converted by data acquisition unit DAS into numerical form and then passed on to calibrator CAL as a respective detector readouts. It has been observed that a certain minimum number of pixels per detector line is required to capture the Moiré pattern. A pixel count of approximately 200 or 250 (in particular 256) has been found to work well.

The respective detector readouts $I_{kl}$, are then fitted at step 615 to the model of equation (1) above. Fitting can be achieved by using least squares or weighted least squares or any other suitable numerical curve fitting technique. For instance, in a least squares approach, equation (1) can be reformulated as an objective function $\Delta^2$ as per $$\Delta^2 = \rho_{k,l}(I_{kl} - A_k(1 + V_k \cos(\kappa k + \varphi_l)))^2 \qquad (2)$$

This is a rather large non-linear fit problem in the three unknowns $A_k$, $V_k$, $\varphi_l$ for the calibration parameters.

The optimization may be performed in one embodiment in several steps in an iterative coordinate decent method, which splits the large problem into several smaller sub-problems, which are easier to solve. In particular, introducing the objective function $\Delta_l^2$ per readout index l, the equation (2) now reads:

$$\Delta_l^2 = \Sigma_k(I_{kl} - A_k(1 + V_k \cos(\kappa k + \varphi_l)))^2 \qquad (3)$$

This is a non-linear fit operation in the three unknowns $A_k$, $V_k$, $\varphi_l$ for the calibration parameters which may be solved by the simplex downhill algorithm or suitable optimization algorithm with non-linear objective (or "cost") function. It will be appreciated, that the above fitting procedure as per equation (3) will need to be repeated for each line detector. This can be done sequentially or preferably in parallel. Also, the fitting operation may commence whilst the scan is progressing and as soon as readouts or available. Alternatively the readouts are collected first and, upon completion of the scan motion, DAS forwards the readouts to calibration module CAL and the fitting then proceeds in sequence or in parallel.

The output at fitting step S615 is a triple of calibration parameters for each pixel k of the respective detector line. The calibration triple for each pixel on a given detector line comprises two pixel dependent parameters: i) the input intensity $A_k$, and ii) the visibility $V_k$. There is also a pixel independent parameter, namely the local Moiré fringe phase $\varphi_l$ for each readout index l.

In an alternative embodiment, a different, more detailed signal model function is used instead. The model function used in Eq. 1 is simply a pure sinusoidal variation of the Moiré fringe. If the gratings of the interferometer are not perfectly flat, there might be deviations from this ideal model. More complex models, possibly with heuristic parameters can be used to model the measured data in such a situation. One particular set of additional parameters that have been implemented are pixel specific mean pixel positions within the detector line as per:

$$I_{kl} = A_k(1 + V_k \cos(\kappa(k + \Delta_k) + \varphi_l)) \qquad (4)$$

Basically, the model is a refinement over the model as per equation 1 which allows for deviations from the perfect sinusoidal shape by assuming that the detector pixels are displaced along their respective detector line by a fixed fraction $\Delta_k$ of the nominal pixel spacing (which is in one embodiment in the order of 50 microns but this a non-limiting example only). Of course, this is only an "interpretation" of parameter $\Delta_k$, which does not necessarily represent the true cause of the deviation. In fact, a grating imperfection may lead to a phase shift of the Moiré pattern, which can be well represented by the parameter $\Delta_k$, too. When using signal model function according to equation 4 instead of equation 4, one fits variables, namely the three variables $A_k$, $V_k$, $\varphi_l$ as before and the displacement parameter $\Delta_k$. Fitting by downhill simplex or other suitable optimization technique is as explained above for equation 4 where now the cosine term is replaced by the term $\cos(\kappa(k+\Delta_k)+\varphi_l)$.

Once the calibration parameters $A_k$, $V_k$, $\varphi_l$ are obtained (if the refined model (4), there are also the fitted pixel displacements $\Delta_k$) by the optimization operation, they can be held in storage and can then be applied to a following object scan data as will now be explained in more detail below when turning to the operation of Reconstructor RECON.

At step 620a an object scan is carried out. Again the detector readouts are passed on, but this time to reconstructor RECON via a switch SW.

To better understand the operation of the phase retrieval step to be carried in step 625 it may be worth observing that calibration module CAL operation was not encumbered by the redundancy in respective of same geometrical array as observed earlier. As will be appreciated, the previous computations through to step S620a proceeded in a detector-line-wise fashion, where each triple of calibration parameters got assigned to each pixel k per readout l. This "processing line-wise" context is no longer applicable for the phase retrieval step. Instead, the processing context for phase retrieval is all data belonging to the same geometrical ray. This is because in order to produce a pixel in the phase contrast image to be reconstructed it will be necessary to collect all those detector measurements that contribute to the pixel in the image that is to represent the accumulated phase shifts along said geometrical path. The accumulated phase shifts then form a projection point that serves as image contrast. This collection-per-geometrical ray operation can be done by operation of a data grabber that evaluates the "spatial stamps" for each readout and collects the pixel-readouts into groups per geometrical array.

Phase retrieval is performed for each geometrical ray independently. Let us denote the number of measurements for a given ray by n. Furthermore, the pixels contributing to this geometrical ray have the calibration parameters $A_i$, $V_i$, and $\beta_i = \kappa(i+\Delta i)+\varphi_l$ or $\beta_i = \kappa i + \varphi_l$ (depending whether model 1a or 1 has been used) as previously determined in the calibration step. The actual measurements of the pixels obtained during the object scan are denoted by $g_i$. The influence of the object BR onto the measured data is modeled by the three image parameters B (the attenuation of the x-ray beam), S (the loss of visibility of the interference pattern due to small angle scattering, this is also called the dark field), and $\varphi$ the beam the phase shift due to refraction which corresponds (after a possible scaling) to the actual phase contrast image to the reconstructed. The other image parameters for the absorption image and the dark field may or may not be required in further processing or display.

These image parameters B, S, $\varphi$ per geometrical ray (that is, image grid point) are estimated by minimizing the cost function:

$$\Delta^2 = \Sigma_{i=1}^n (g_i - BI_i(1 + SV_i \cos(\beta_i + \varphi)))^2 \qquad (5)$$

This is a non-linear fit in the three unknowns which is may be solved again by the simplex downhill algorithm or other suitable optimization algorithm as explained earlier in connection with the fitting step of the calibration module CAL. The output at step S620 is, for each geometrical ray, a respective image point that collectively (taken over all geometrical rays) define the resulting images for the attenuation, loss of visibility and differential phase.

At step S630 the resulting images for attenuation and/or loss of visibility and/or differential phase are then output and can then be rendered for display on monitor MT or otherwise image processed.

There is also an optional artifact correction step 620b implemented by correction module CORR. Applicants has observed on occasion certain artifacts in the reconstructed image. More specifically, the main structure of the artifacts follows still the Moiré pattern. The origin of these artifacts is the fact that even with the augmented signal model as per Eq. (4), the blank scan is not modeled with sufficient accuracy. To combat these drift artifacts, a concept of artifact cancellation is proposed herein as outlined in the following. It has been further observed that the artifacts that present themselves in the differential phase image obtained in particular with the augmented model as per Eq. (4) are well reproduced if we use the blank scan as an object scan. In other words, the calibration parameters themselves are treated in step S20b as if they were obtained from an "object" scan by performing a phase retrieval operation analogous to step S625. In other words, the calibration parameter triple is grouped by grabber into groups per geometrical ray as has been explained earlier for the "real" phase retrieval step S625 based on object scan data. The respective images of absorption, dark field and phase shift can be considered respective correction images; that is an absorption correction image, a dark field correction image and a phase contrast correction image. Again, this operation of treating the blank scan as an object scan by performing a phase retrieval operation on the blank scan calibration data is very much counterintuitive as the calibration data in and of itself is normally not envisaged for display and phase retrieval operation is usually carried out precisely to obtain images for display. Now, having observed that we can reproduce some artifacts with this additional blank scan for object scan processing, it is proposed herein to supply this correction image back to the image reconstructor and to cancel out these artifacts by subtracting this "pure" artifact correction image from the true object image obtained during phase retrieval. In other words, the correction image is used when performing a phase retrieval operation on object image data. In one embodiment the application of the correction image is according to $$\tilde{B} = \frac{B}{B'}, \tilde{V} = \frac{V}{V'},$$

$\tilde{\varphi} = \varphi - \varphi'$, where $B'$, $V'$, $\varphi'$ are the respective correction images and $B$, $V$, $\varphi$ are the absorption, dark field, and phase contrast images obtained from the phase retrieval step on object scan readouts with "tilde" indicating the respective corrected versions.

In order to avoid the introduction of additional noise by the artifact cancellation step, the artifact image is slightly low-pass filtered in scan direction.

The effect of the different processing steps, i.e., the improved modeling of the fringe pattern as per equations 1 and 1a and the artifact cancellation in step 620b have been illustrated here using the differential phase contrast images only. For the attenuation contrast image and the visibility image, similar improvements can be obtained.

In one embodiment, the components of image data processing system IDP as per FIG. 1 all run on a single computing system like the imaging apparatus' MA workstation WS. In an alternative embodiment an at least partly distributed architecture is likewise envisaged herein where one or more of the components are located remotely and are connected with each other and/or with the image data processing system IDP in a suitable communication network.

In one embodiment, image data processing system IPD (or at least some of its components) is arranged as a dedicated FPGA or as a hardwired (standalone) chip.

The components of image data processing system may be programmed in a suitable scientific computing platform such as Matlab® and may be translated into C++ or C routines suitable to run on a computing system (such as the imager's workstation WS).

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above-described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A phase contrast radiography system of the scanning type, comprising:
    a pedestal;
    an arm movable relative to the pedestal;
    in a mounting in or at the arm, an interferometer assembly including one or more gratings;
    an X-ray source for generating radiation;
    a detector, mounted in or at the arm, movable in a scanning motion for receiving said radiation after interaction of said radiation with the interferometer gratings to produce a drifting Moiré intensity pattern detectable by the detector across a sequence of readouts when the apparatus is in use;
    a rigidizer operable to apply a force upon the arm and/or the interferometer mounting to vary prior or during said scanning motion the rigidity thereof so as to impart a relative motion between the at least two gratings thereby affording the ability to vary the local fringe phase of said Moiré pattern.

2. Phase contrast radiography system according to claim 1, wherein the rigidizer is arranged as clamp actuator with at least one pair of jaws for engagement therebetween of the arm and/or the interferometer assembly so as to allow selectably adjusting an amount of the applied force so as to achieve a desired amount of drifting of the Moiré pattern.

3. Phase contrast radiography system according to claim 1, wherein the rigidizer is manually operable.

4. Phase contrast radiography system according to claim 2, wherein the clamp actuator includes a micrometer arrangement with one or more calipers operable to engage the mounting so as to allow a user to selectably adjust in discrete steps an amount of the applied force.

5. Phase contrast radiography system according to claim 1, wherein the rigidizer is formed from a bimetallic sheet attached to the arm and or the interferometer mounting.

6. Phase contrast radiography system according to claim 5, comprising a video signal generator to supply the sequence of readouts to a display unit during operation of the rigidizer so as to achieve a visual rendering of how the Moiré phase varies with the applied force.

7. Phase contrast radiography system according to claim 6, comprising:
    a calibration module configured to:
        receive the sequence of detector readouts;
        fit the readouts to a measurement signal model function by solving for a plurality of calibration parameters including a plurality of phases of the drifting Moiré pattern and/or at least one of intensity per pixel and visibility per pixel.

8. Phase contrast radiography system according to claim 1, wherein the system is mammography scanner system or a computed tomography scanner system.

9. A method for processing data supplied by a phase contrast radiography apparatus of the scanning type including an interferometer, the method comprising:
    receiving a sequence of detector readouts that together record a drifting Moiré pattern, wherein the readouts are detected by a plurality of detector pixels of a detector of said apparatus during a blank scan operation, wherein the drift is caused by relative motion between at least two gratings of said interferometer during said scan operation;
    fitting the readouts to a measurement signal model function by solving for a plurality of calibration parameter including a plurality of phases of the drifting Moiré pattern and/or at least one of intensity per pixel and visibility per pixel; and
    adjusting the rigidity of the arm and/or of the mounting of the interferometer so as to control the drift in the Moiré pattern.

10. Method according to claim 9, wherein the fitting operation includes solving for a pixel displacement per pixel.

11. Method according to claim 9, further comprising applying a phase retrieval operation to the detector readouts for the blank scan to produce at least one corrector phase contrast image.

12. Method according to claim 9, comprising:
    scanning an object to be imaged to obtain detector readouts for the object;
    using the at least one corrector phase contrast image in applying a phase retrieval operation to the object detector readouts to obtain a phase contrast image of the object.

13. A non-transitory computer-readable medium having one or more executable instructions stored thereon, which when executed by a processor, cause the processor to perform a method for processing data supplied by a phase contrast radiography apparatus of the scanning type including an interferometer, the method comprising:
    receiving a sequence of detector readouts that together record a drifting Moiré pattern, wherein the readouts are detected by a plurality of detector pixels of a detector of said apparatus during a blank scan operation, wherein the drift is caused by relative motion between at least two gratings of said interferometer during said scan operation;
    fitting the readouts to a measurement signal model function by solving for a plurality of calibration parameter including a plurality of phases of the drifting Moiré pattern and/or at least one of intensity per pixel and visibility per pixel; and
    adjusting the rigidity of the arm and/or of the mounting of the interferometer so as to control the drift in the Moiré pattern.

* * * * *